United States Patent

Hanke

Patent Number: 5,112,884
Date of Patent: May 12, 1992

[54] DENTAL FILLING MATERIAL

[75] Inventor: Bernhard Hanke, Schwalbach, Fed. Rep. of Germany

[73] Assignee: The Procter & Gamble Company, Cincinnati, Ohio

[21] Appl. No.: 474,413

[22] Filed: Feb. 2, 1990

[51] Int. Cl.$^5$ .......................... A61K 5/01; C08K 3/22
[52] U.S. Cl. .................... 523/116; 523/109; 433/228.1; 106/438; 501/8; 501/32; 501/73; 526/241
[58] Field of Search ................ 523/109, 116; 433/228.1; 106/438; 501/8, 32, 73; 526/241

[56] References Cited

U.S. PATENT DOCUMENTS 3,801,344  4/1974  Dietz ..................... 106/300
3,975,203  8/1976  Dietz ..................... 106/299

Primary Examiner—Paul R. Michl
Assistant Examiner—T. McDonald, Jr.
Attorney, Agent, or Firm—Kim William Zerby; Douglas C. Mohl; Richard C. Witte

[57] ABSTRACT

The invention relates to a dental filling material containing at least one polymerizable (meth)-acrylic acid ester, characterized in that it contains 20 to 90% by weight, calculated on the total composition, of a compound consisting of the structural element E2 and at least one of the structural elements E1 and/or E3 and/or E4 of the general formula

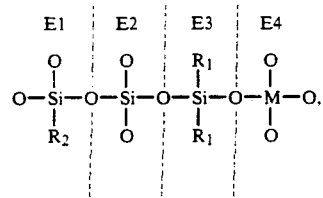

where $R_1$ denotes a methyl, ethyl, n-propyl, isopropyl or an unsubstituted or $CH^3$—$C_3H_7$—substituted phenyl radical, $R_2$ denotes a $CH_2=CH-$, $CH_2=CHCOO(CH_2)_n-$]or $$CH_2=C-COO(CH_2)_a\text{-radical}$$
$$|$$
$$CH_3$$

or $R_1$, n denotes 0, 1, 2 or 3, and M denotes titanium or zirconium.

6 Claims, No Drawings

DENTAL FILLING MATERIAL

The present invention relates to a novel dental filling material which contains a specific filler.

Dental restorative materials based on polymerizable compounds, so-called composites, contain obligatorily a mineral filler in addition to one or more polymerizable monomers, especially (meth)acrylic acid esters, activators, optionally polymerization catalysts and other components.

Depending on the type and amount, this filler determines the physical properties of the filling made using the composite. The greater the filler content and the larger the particle size, the better it is for the physical properties but usually the worse for the polishability of the filling.

A need therefore arose to develop dental filling materials which not only have good physical properties but can be also satisfactorily polished.

This object is achieved in that dental filling materials based on otherwise customary components, especially at least one polymerizable (methy)acrylic acid ester, contain 20–90 percent by weight, calculated on the total composition, of a compound consisting of the structural element E2 and at least one of the structural elements E1 and/or E3 and/or E4 of the general formula

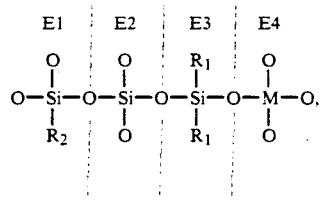

where $R_1$ denotes a methyl, ethyl, n-propyl, isopropyl or an unsubstituted or $CH_3$–$C_3H_7$-substituted phenyl radical, $R_2$ denotes a $CH_2$=CH–, $CH_2$=CHCOO(CH$_2$)– or

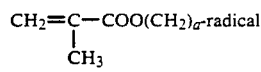

or $R_1$, n denotes 0, 1, 2 or 3, and M denotes titanium or zirconium.

By using these organically modified silica compounds as fillers not only is outstanding polishability of the composites achieved, but also the physical properties, especially the mechanical strength and abrasion resistance of the fillings, are very substantially improved.

The structural unit E2 of the above general formula is present in combination with at least one of the structural units E1, E3 or E4, in which case the preferred molar ratio of E2 to the other structural elements is between 50:1 and 10:1, preferably between 30:1 and 20:1, particularly about 25:1.

If the compound consists of more than two structural elements, the ratio of E2 to E1 and E3 likewise is preferably between 50:1:1 and 10:1:1, particularly 30:1:1 and 20:1:1; the same is of course also true with regard to the combination E2/E1/E4 or E2/E3/E4.

If all the structural elements of the general formula are present together, then the molar ratio of the structural elements E2:E1:E3:E4 is between 50:1:1:1 and 10:1:1:1, preferably between 30:1:1:1 and 20:1:1:1, particularly about 25:1:1:1.

Examples of suitable compounds are the following:

E2:E1 = 50:1

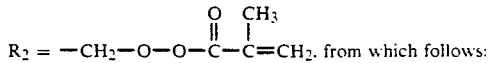

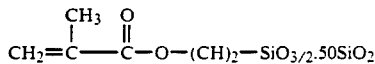

or

E2:E3 = 25:1
$R_1$ = $CH_3$, from which follows:
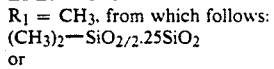
or
E2:E3:E4 = 25:1:1
$R_1$ = $CH_3$
M = Zr, from which follows:
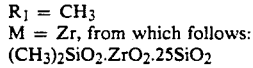

These inorganic-organic polymers are basically known from the prior art and are designated inter alia as "ORMOCER" or "ORMOSIL".

They are described, for example, in the 1987 activities report of the Fraunhofer-Institut für Silikatforschung, Würzburg, pp. 48–74, and in a survey published in "Bild der Wissenschaft" No. 11/1987, p. 29.

These polymers are prepared by the sol-gel process in the presence of an acid or basic catalyst in alcoholic or aqueous alcoholic solution at about 25° to about 300° C. by reacting a tetraalkoxysilane, for example tetraethoxysilane, with (meth)acryloxypropyltrimethoxysilane and, if desired, a tetraalkoxyzirconium or tetraalkoxytitanium and, if desired, dialkyldialkoxysilane.

It is necessary to keep the amount of hydroxysilane groups as low as possible, which can be achieved by adjusting the corresponding pH.

The halides of the corresponding silanes may be also expediently employed as starting products. The resultant reaction product is separated from the reaction solution, dried at about 100° C. to about 500° C. and ground.

Should the amount of SiOH groups be undesirably high, these can be completely removed by a basic postcondensation or by additional silylation using, for example, (meth)acryloxypropyltrimethoxysilane.

The preparation of the ORMOCERs may be generally expressed as follows: reaction of an alkoxysilane $Si(OR_1)_4$ with an alkoxysilane $R_2$–$Si(OR_1)_3$ and/or an alkoxysilane $(R_1)_2$–$Si(OR_1)_2$ and/or a metal ester $M(OR_1)_4$, $R_1$, $R_2$ and M having the meaning defined above.

The surface of the ORMOCERs used according to the invention as fillers is between about 10 and about 50 m$^2$/g, particularly 20–30 m$^2$/g.

The ORMOCER fillers used according to the invention may be the only filler comprised in the dental filling materials, but it appears expedient to combine these with other fillers known per se.

The total filler content in the dental filling materials according to the invention is between about 55 and not more than 90 percent by weight based on the total composition, preferably between about 65 and about 85 percent by weight.

Suitable fillers to be used in combination with the ORMOCERs and known per se, are preferably silylated silicon dioxides, for example of the "Aerosil" type, the various boron and barium silicate glasses, aluminium silicate and glass ceramic fillers etc., such as disclosed, for example, in U.S. Pat. Nos. 3,801,344, 3,808,370 and 3,975,203 and in DE-A 2,347,591.

A suitable precipitated or pyrogenic silicon dioxide, a so-called microfiller, is disclosed, for example, in DE-A 2,403,211 and EP-A 60,911.

The dental filling materials according to the invention are particularly suitable for use as light-curing products, i.e. products which are present in a single phase and polymerize under the influence of light.

Such compositions contain one or more photopolymerization initiators. Suitable compositions are particularly carbonyl compounds such as benzoin and its derivatives, particularly benzoin methyl ether, benzil and benzil derivatives, for example 4,4-oxydibenzil and other dicarbonyl compounds, for example diacetyl, 2,3-pentanedione or metal carbonyls, quinones, particularly camphorquinone, or their derivatives. The proportion of the photopolymerization initiator is about 0.01 to about 5% by weight based on the total composition.

These light-curable, i.e. photopolymerizable preparations preferably also contain so-called polymerization accelerators. These are substances which speed up the polymerization reaction in the presence of polymerization initiators. Examples of known accelerators are amines such as p-toluidine, N-N-dimethyl-p-toluidine, N,N-di(hydroxyethyl)-p-toluidine, trialkylamines such as trihexylamine, polyamines such as N,N,N',N'-tetraalkylalkylenediamines, barbituric acid and dialkylbarbituric acids and sulphimides, preferably in an amount of about 0.01 up to about 5% by weight based on the total composition.

Suitable accelerators are described, for example, by G. M. Brauer et al., Journal of Dental Research, Vol. 58, No. 10 (1979), pp. 1994–2000.

It is of course also possible to use the dental filling materials according to the invention in the form of a two-phase preparation, one phase containing a polymerization catalyst, for example a peroxide, and the other phase containing an accelerator for this peroxide, for example an organic amine, in which case the two phases are mixed immediately prior to the tooth being filled and the polymerization occurs in the drilled cavity to be filled, which is preferably provided with a lining or bonding material.

Suitable peroxides which decompose at the start of the polymerization forming radicals, are, for example, aryl peroxides such as benzoyl peroxide, cumene hydroperoxide, urea peroxide, tert-butyl hydroperoxide or tert-butyl perbenzoate and silyl peroxides, preferably in amounts from about 0.01 to about 5, particularly about 0.5 to 2.5% by weight based on the total composition.

If one phase of the two-phase agent contains a polymerization initiator, then an accelerator of the type described above, preferably an amine, or barbituric acid or its derivatives, for example a dialkylbarbituric acid, is expediently added to the other phase.

Basically any suitable compounds suggested for this purpose may be used as a polymerizable monomer in the dental filling materials according to the invention. Such compounds are particularly the known products obtained by reacting bisphenols, particularly bisphenol A, with glycidyl methacrylate, known under its abbreviation of bis-GMA, the various alkanediol dimethacrylates such as 1,6-hexanediol methacrylate, 1,4-butanediol dimethacrylate, triethylene or tetraethylene glycol dimethacrylate, bis(2-methacroylpropyl) phthalate, isophthalate or terephthalate, trimethylolpropane dimethacrylate and trimethacrylate, as well as particularly the reaction products obtained by diisocyanates and hydroxyalkyl methacrylates, such as are described, for example, in DE-A 2,312,559, adducts from (di)isocyanates and 2,2-propane-bis[3-(4-phenoxy)-1,2-hydroxypropane] 1-methacrylate according to US-A 3,629,187 and the adducts of isocyanates and methacryoyl alkyl ethers, methacroyl alkoxy benzenes and methacroyl alkoxy cycloalkanes, such as described in EP-A 44,352.

It is of course also possible to use mixtures of suitable monomers.

It is also expedient to use at the same time, as a component of the mixture of monomers, small amounts of brominated methacrylic acid esters, such as those described in EP-A 143,362, in order to improve the opacity to X-rays of the filling.

It is finally expedient to add UV stabilizers to the dental filling materials based on synthetic resins in order to prevent darkening during the ageing of the fillings. A particularly suitable UV stabilizer is 2-hydroxy-4-methoxybenzophenone. Another preferred material is 2-(2'-hydroxy-5'-methylphenyl)benzotriazole; but basically any physiologically inert UV absorbent is suitable for this purpose. Suitable examples are, inter alia, hydroquinone, p-benzoquinone and p-butylhydroxytoluene. The last-mentioned compound may also act in the filling as, for example, an antioxidant.

A survey of the substances conventionally used in dental filling materials can be found in the paper by R. L. Bowen in Journal of Dental Research, Vol. 58/5 (May 1979), pp. 1493–1503, and in the immediately following supplementary paper by J. F. Lann, pp. 1504–1506.

To obtain an appearance as natural as possible of the filled areas of the teeth, the composite materials necessarily also contain a small amount of dyes or pigments.

The examples below serve to elucidate further the invention.

PREPARATION OF THE FILLERS

EXAMPLE A

An ethanolic solution of 1000 g (4.8 mol) of Si(OC$_2$H$_5$)$_4$ and 24.8 g (0.1 mol) of methacryloxypropyltrimethoxysilane is stirred under reflux. 500 ml of strength NH$_3$ solution are added dropwise to the boiling solution. After stirring for 30 minutes the precipitate is treated with water and stirring is continued for a further 4 hours. The cooled precipitate is filtered off, again treated with 500 ml of NH$_3$ solution and introduced into a glandless reaction vessel to undergo a post-reaction. The washed precipitate is dried in a rotary drier in an atmosphere of argon and is then ground.

EXAMPLE B

An ethanolic solution of 1000 g (4.8 mol) of Si(OC$_2$H$_5$)$_4$ and 29.8 g (0.2 mol) of (CH$_3$)$_2$Si(OC$_2$H$_5$)$_2$ is stirred under reflux. 500 ml of a 5% strength NH$_3$ solution are added at boiling temperature. After stirring for 30 minutes the forming precipitate is treated with water and stirring is continued for a further 4 hours. The cooled precipitate is filtered off, again treated with 500 ml of NH$_3$ solution and introduced into a glandless reaction vessel for post-condensation. The washed precipitate is dried in a rotary drier in an atmosphere of argon and is then ground.

EXAMPLE C

An ethanolic solution of 1000 g (4.8 mol) of Si(OC$_2$H$_5$)$_4$, 32.7 g (0.1 mol) of Zr(OC$_3$H$_7$)$_4$ and 14.9 g (0.1 mol) of (CH$_3$)$_2$Si(OC$_2$H$_5$)$_2$ is stirred under reflux. 500 ml of a 5% strength NH$_3$ solution are added at boiling temperature. After stirring for 1 hour the forming precipitate is treated with water and stirring is continued for a further 6 hours. The cooled precipitate is filtered off, again treated with 500 ml of NH$_3$ solution and introduced into a glandless reaction vessel for postcondensation. The washed precipitate is dried in a rotary drier in an atmosphere of argon and is then ground.

PREPARATION OF THE COMPOSITES

EXAMPLE 1

| | |
|---|---|
| Filler from Example A | 70.00 g |
| 1,12-Dodecanediol dimethacrylate | 6.28 g |
| 2,2-Bis[4'-(2"-methacroylethoxy)phenyl]propane | 23.26 g |
| 4-Methoxyphenol | 0.005 g |
| Ethylbenzoin | 0.10 g |
| Camphorquinone | 0.16 g |
| 2-n-Butoxyethyl 4-(dimethylamino)benzoate | 0.18 g |
| Butylhydroxytoluene | 0.005 g |

EXAMPLE 2

| | |
|---|---|
| Filler from Example B | 69.00 g |
| 1,12-Dodecanediol dimethacrylate | 6.5 g |
| 2,2-Bis[4'-(2"-methacroylethoxy)phenyl]propane | 25.05 g |
| 4-Methoxyphenol | 0.005 g |
| Ethylbenzoin | 0.10 g |
| Camphorquinone | 0.16 g |
| 2-n-Butoxyethyl 4-(dimethylamino)benzoate | 0.18 g |
| Butylhydroxytoluene | 0.005 g |

EXAMPLE 3

| | |
|---|---|
| Filler from Example C | 73.00 g |
| 1,12-Dodecanediol dimethacrylate | 5.64 g |
| 2,2-Bis[4'-(2"-methacroylethoxy)phenyl]propane | 20.90 g |
| 4-Methoxyphenol | 0.005 g |
| Ethylbenzoin | 0.10 g |
| Camphorquinone | 0.16 g |
| 2-n-Butoxyethyl 4-(dimethylamino)benzoate | 0.18 g |
| Butylhydroxytoluene | 0.005 g |

Following curing using a conventional light source, the following physical values were measured:

| | Composite from Example | | | Comparison (commercial product) |
|---|---|---|---|---|
| | 1 | 2 | 3 | |
| Bending strength (N/mm$^2$) | 115 | 112 | 117 | 60 |
| Modulus of elasticity (N/mm$^2$) | 6,400 | 6,900 | 4,600 | 3,600 |

The polishability of the resultant polymers was outstanding.

What is claimed is:

1. Dental filling material containing at least one polymerizable (meth)acrylic acid ester, characterized in that it contains 20 to 90% by weight, calculated on the total composition, of a compound consisting of the structural element E2 and at least one of the structural elements E1 and/or E3 and/or E4 of the general formula

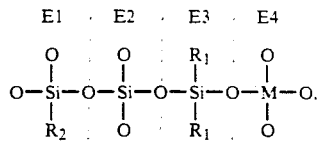

where R$_1$ denotes a methyl, ethyl, n-propyl, isopropyl or an unsubstituted or CH$_3$—C$_3$H$_7$-substituted phenyl radical, R$_2$ denotes a CH$_2$=CH—, CH$_2$=CHCOO(CH$_2$)$_n$— or
or R$_1$,

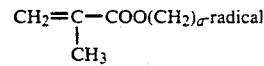

n denotes 0, 1, 2 or 3, and M denotes titanium or zirconium; and wherein further the molar ratio of the structural element E2 to the structural element E4, if present, is greater than 10:1.

2. Dental filling material according to claim 1, characterized in that the molar ratio of the structural element E2 to the structural elements E1 and/or E3 and/or E4 is in each case between 50:1 and 10:1.

3. Dental filling material according to claim 2, characterized in that the molar ratio of the structural element E2 to the structural elements E1 and/or E3 and/or E4 is in each case between 30:1 and 20:1, particularly about 25:1.

4. Dental filling material according to claim 2, characterized in that the molar ratio of the structural elements E2:E1:E3:E4 is about 25:1:1:1.

5. Dental filling material containing at least one polymerizable (meth)acrylic acid ester, characterized in that it contains 20 to 90% by weight, calculated on the total composition, of a compound consisting of the structural element E2 and at least one of the structural elements E1 and/or E3 of the general formula:

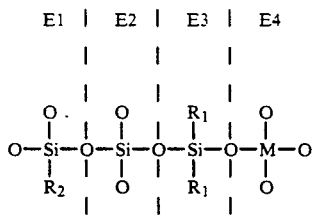

where R$_1$ denotes a methyl, ethyl, n-propyl, isopropyl or an unsubstituted or CH$_3$—C$_3$H$_7$—substituted phenyl radical, R$_2$ denotes a CH$_2$=CH—,

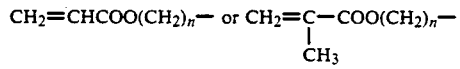

radical or R$_1$, n denotes 0, 1, 2 or 3, and M denotes titanium or zirconium.

6. A method of restoring tooth surfaces, said method comprising applying to a tooth in need of restoration a dental composition according to claim 1.

* * * * *

UNITED STATES PATENT OFFICE
CERTIFICATE OF CORRECTION

PATENT NO. : 5,112,884

DATED : May 12, 1992

INVENTOR(S) : Bernhard Hanke

It is certified that error appears in the above-identified patent and that said Letters Patent is hereby corrected as shown below:

Column 4, line 49, "500 ml of strength" should read
-- "500 ml of a 5% strength" --

Signed and Sealed this

Twenty-ninth Day of June, 1993

Attest:

MICHAEL K. KIRK

*Attesting Officer*    *Acting Commissioner of Patents and Trademarks*